United States Patent

Nadasy et al.

[11] 4,218,234
[45] Aug. 19, 1980

[54] SOIL CONDITIONERS

[75] Inventors: Miklós Nadasy; Miklós Kovács; Márton Kólcsei; János Vad; Béla Bartha; Ottó Dobozy; Ferenc Máté; Éva Karácsonyi née Spindler, all of Budapest, Hungary

[73] Assignee: Novex Rt., Budapest, Hungary

[21] Appl. No.: 829,740

[22] Filed: Sep. 1, 1977

Related U.S. Application Data

[63] Continuation-in-part of Ser. No. 790,247, Mar. 25, 1977, abandoned, which is a continuation of Ser. No. 422,888, Dec. 1, 1973, abandoned.

[30] Foreign Application Priority Data

Dec. 7, 1972 [HU] Hungary .............................. EE 2074

[51] Int. Cl.$^2$ .......................... A01N 5/00; A01N 7/00
[52] U.S. Cl. .................... 71/86; 71/DIG. 1; 71/113; 71/118; 71/88; 71/92; 71/94
[58] Field of Search ..................... 71/DIG. 1, 118, 86, 71/113

[56] References Cited

PUBLICATIONS

Schwarz et al., Surface Active Agents and Detergents, Interscience Publishers, New York, 1958, vol. I, pp. 151–200, vol. II, pp. 103–120 and pp. 166–171.

*Primary Examiner*—Catherine L. Mills

[57] ABSTRACT

A cationactive soil-conditioning composition which comprises one or more active ingredients having the formulae

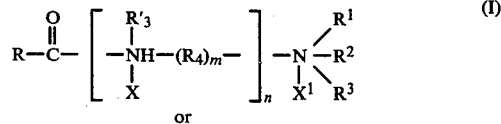

(I)

or

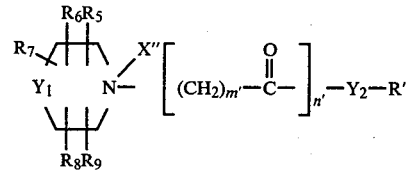

(II)

or

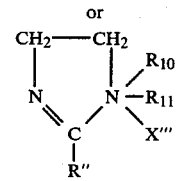

(III), wherein R is a $C_{10-24}$ linear or branched alkyl, alkenyl or alk-dienyl group; $R_1$ is hydrogen, $R_2$ is hydrogen, $C_{2-18}$ as a linear or branched alkyl, alkenyl, alk-dienyl or $C_{2-18}$-alpha-keto-group, $R_3$ is a hydrogen; $R_3'$ if present is hydrogen or $C_{1-8}$ alkyl; X and X' are formiate, acetate, propionate, hydrophosphate, hydroxyl, halogenide or nitrate; $R_4$ methylene, ethylene or a polyglycol ether-group; m is a cardinal number from 1–6 and n is an integer from 1–6; R' is $C_{10-24}$ linear or branched alkyl, alkenyl or alk-dienyl; $R_5$, $R_6$, $R_7$ if present, is a hydrogen or taken together two substituents therefrom a CH=CH—CH=CH— group; $R_8$, $R_9$, if present, hydrogen or methyl; $Y_1$ is a —CH= or oxygen; $Y_2$ is —NH— or oxygen; X" is halogenide, acetate, nitrate, sebacate, tartarate. propionate, phosphate, hydrogenphosphate, carbonate, hydrogencarbonate or formiate; m' is a cardinal number from 1–6; m' is an integer from 1–6; $R_{10}$ and $R_{11}$ are independently from each other hydrogen, ethyl, propyl, oxyethyl, oxypropyl, aminoethyl or aminopropyl-groups; R" is $C_{9-24}$ linear or branched alkyl or alkenyl; X'" is nitrate, halogenide, formiate acetate, propionate or butyrate.

There is also provided a process for improving the crop-bearing characteristics of soil, in which a composition containing the above active ingredient, is added to soil.

3 Claims, No Drawings

SOIL CONDITIONERS

This is a continuation in part of application Ser. No. 790,247, filed on Apr. 25, 1977 which is a continuation of Ser. No. 422,888, filed on Dec. 7, 1973, both now abandoned.

The present invention relates to cationactive soil conditioners for promoting plant growth and yield.

The fostering of growth and increasing of yield of useful plants can be accomplished partly by positive influences on the plants themselves and partly by the partial or complete destruction of the plant and/or animal organisms which limit or inhibit the development of useful plants. In other cases the limitation or fostering of such plant or animal organisms can prove beneficial to growth of useful plants. Small amounts of nitrogen-containing organic compounds are often added to fertilizers for promoting plant growth by positive influences. Organic acids can be used, for example, as biological growth promoters; also hormones, e.g. Auxin and Giberellinic acid.

S. E. Seymour and others have shown (Symposium of the American Society of Agronomy, Dallas, 1953) that in some cases certain anionic and nonionic surfactants promote plant growth. The effect of the anionic and nonionic materials was explained by G. G. Shepchenko, N. L. Shepchenko and J. M. Volkov (Lesnoye Hozyaystvo No. 6, pp. 35-36, 1970), and by others, in that anionic or nonionic surfactants reduce surface tension and increased plant growth is brought about through the resulting increased diffusion. Reduction of the surface tension promotes the penetration of water and nourishing materials into the root system of the plant and thus accelerates its growth.

It has been observed that stimulating activity of the above-mentioned nonionic and anionic detergents is not unequivocal, because, depending on the circumstances, such materials can also act as inhibitors. The partly stimulating, partly inhibiting and even phytotoxic activity often varies, therefore and anionic and nonionic surfactants are not very widely used for the growth stimulation of plants.

The growth of useful plants can also be promoted by the partial or total destruction of the plant or animal organisms which detrimentally affect plant growth. Herbicides, fungicides, insecticides and germicides are generally cationic compounds or are compounds which can be converted into cationic compounds. Members of this group include azines, such as phenazine, thiazine- and oxazine derivatives, piperidyl- and nicotine derivatives, biguanide derivatives and various quaternary ammonium salts. Quaternary ammonium halogenide such as alkylpyridinium compounds, are widely used as microbicidal agents. According to prevailing expert opinion, however, these materials tend to retard plant growth and possess phytotoxic properties. There are a few cationactive detergents being used in agriculture, which have slight phytotoxic activity and are employed to fight mushrooms. The information which is available about the growth-controlling activity of cationic surfactants, is pronouncedly of a negative character and, therefore such agents are employed at most only as auxiliary agents for the distribution of other materials in the ground or by spraying onto plants. No experiments have been performed to determine the mechanism by which cationic detergents or materials which can be converted into cationic detergents act in promoting plant growth, because the prior art held forth no promise for the utilization of such materials for such purposes.

We have found that the following cationic materials, and tensides which can be converted into these materials, surprisingly proved themselves effective as promoters of plant growth. The soil-conditioning materials in accordance with the present invention contain at least one of the following active ingredients

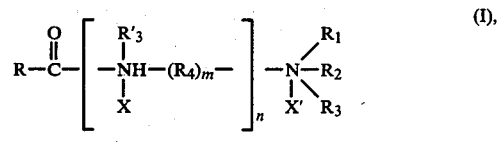

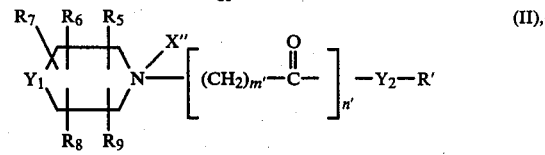

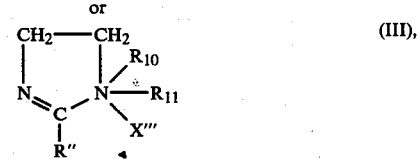

a linear acid-amide derivative according to the general formula (I), an N-heterocyclic compound according to the general formula (II), or an imidazolin or imidazolinium derivative according to the general formula (III), wherein R is a $C_{10-24}$ linear or branched alkyl, alkenyl or alk-dienyl-group; $R_1$ is hydrogen, $R_2$ is hydrogen, $C_{2-18}$ is a linear or branched alkyl, alkenyl, alk-dienyl or $C_{2-18}$-alpha-keto-group, $R_3$ is a hydrogen; $R_3'$ if present is hydrogen or $C_{1-8}$ alkyl; X and X' are formiate, acetate, propionate, hydrophosphate, hydroxyl, halogenide or nitrate; $R_4$ methylene, ethylene or polyglycol ether-group; m is a cardinal number from 1-6 and n is an integer from 1-6; R' is $C_{10-24}$ linear or branched alkyl, alkenyl or alkdienyl; $R_5$, $R_6$, $R_7$ if present is a hydrogen or taken together two substituents therefrom a CH=CH—CH=CH— group; $R_8$, $R_9$, if present, hydrogen or methyl; $Y_1$ is a —CH= or oxygen; $Y_2$ is —NH— or oxygen; X'' is halogenide, acetate, nitrate, sebacate, tartarate, propionate, phosphate, hydrogenphosphate, carbonate, hydrogencarbonate or formiate; m' is a cardinal number from 1-6; m' is an integer from 1-6; $R_{10}$ and $R_{11}$ are independently from each other hydrogen, ethyl, propyl, oxyethyl, oxypropyl, aminoethyl or aminopropyl-groups; R'' is $C_{9-24}$ linear or branched alkyl or alkenyl; X''' is nitrate halogenide, formiate acetate, propionate or butyrate.

The aforementioned active ingredients in accordance with the present invention, of formulae I, II, and III, can be prepared, for example, by methods described in literature sources such as A. M. Schwarz, J. W. Perry, and J. Berch: Surface Active Agents and Detergents, Interscience Publishers, New York 1958, Vol. I., pp. 151-200, Vol. II, pp. 103-120 and pp. 166-171; and K. Lindner: Tenside, Textilhilfsmittel, Waschrohstoffe, Wissenschaftliche Verlagsgesellschaft, Stuttgart, Vol. I (1964), pp. 965-1025, 1058-1061, Vol. III (1971), pp. 2341-2371.

In addition to the above active ingredients, the compositions in accordance with the present invention can also contain reactive tensides, also flocculating agents having a high molecular weight in amounts of 20–80% by weight, such as alginates or their derivatives, cellulose derivatives as carboxymethylcellulose, celluloseethers- or ester, polyacrylates, polyacrylamides, hydrolysed polyacrylonitrile, polyacrylic acid salts, or copolymers of vinylalcohol, copolymers of methacrylic acid and dimethylaminomethacrylate, copolymers of vinylchloroacetate and diammonium maleate, polyvinyl-2-chloroether, copolymers of styrene and methacrylic acid, polyvinylhydrogenphthalates, sulfonated polystyrenes, copolymers of styrene and itaconic acid anhydride, copolymers of vinylacetate and maleic acid anhydride, polyvinylacetate, polyvinylpyridinium, polyvinylalcohol, polyvinylpyrrolidone, polymethacrylic acid, and sulfonated resins.

The compositions of the present invention can also contain anionic and/or nonionic tenside compounds which in certain cases and in certain fields of application increase the activity of the active ingredients.

In other cases it was found to be advantageous also to add to the compositions herbicides, fungicides, germicides and/or insecticides and also soil sterilizing agents.

The compositions of the present invention can be used to treat plants or soil, before or after the appearance of growth above the surface, in preemergent or postemergent conditions.

It is assumed that the active ingredients of the present invention form complexes at the negatively charged locations of minerals in the ground with the available metal ions, and form van der Waals-type bonds with the partial charges. The formation of a bond with the minerals in the soil is significant for the following reasons:

(a) The soil structure and its water- and air content can be beneficially affected. The soil becomes crumbly and the water-holding capacity of the soil clumps increases. In the deeper soil strata the water-conducting capability of the soil can be reduced and in the upper layers evaporation from the soil and attendant drying can be prevented. Thus the useful water-containing capacity of the soil can be increased.

(b) The active ingredients of the compositions of the present invention exert their plant growth-promoting activity only when the active compound is chemically bound, i.e. there is an interaction between the active compounds and certain components of the soil, which increases the yield the crops particularly under dry climatic conditions. The active compounds of the present invention increase the life functions of plants by increasing the absorption of nourishing materials, assimilation, photosynthesis, furthermore, increase the nucleic acid content and the activity of the nucleic acid, as well as the activity of some enzymes. The growth-promoting activity depends on the amount of the active compounds that are employed. The amount of the active ingredients can suitably go as high as 30–100 kg/hectare.

(c) It was also surprisingly found that the active materials which are bound to soil components, beneficially affect the functions of soil bacteria. Bacterial activity increases after the soil is treated, and such increased activity persists for 6–12 weeks. The increase in the activity of soil bacterial acts upon the life functions of the crops and results in an increase of vegetative growth rate and/or an increase in crop yield.

It can be determined that the activity of the active components of the present compositions manifests itself in the end results in a synergistic manner. These results are surprising because heretofore cationactive surfactants were believed not to possess any plant growth-fostering activity, but were known generally to have phytotoxic properties. In accordance with the present invention it was surprisingly contrariwise found that the present cationactive materials exert unequivocally beneficial biological activity which results in increased and in stronger growth.

The active compositions of the present invention can be employed in the form of emulsions or solutions, and also applied to a carrier. In the preparation of liquid spray formulations the concentration of the active ingredient is suitably from about 0.0001 to about 10 g active component/liter of spray liquid. In the case of dusting powder formulations the concentration of the actives is suitably from about 10 to about 80% by weight. Of all varieties of known type of formulations dusting powders and sprays are considered most suitable. In the preparation of dusting powders from liquid compositions suitably a chemically neutral carrier is saturated with the liquid. In the preparation of the powder a suitable carrier should be employed which does not affect the activity of the composition and has to phytotoxic activity with respect to the crops. Suitably minerals such as diatomaceous earth, chalk, bentonite, kaolinite, quartz powder, or organic materials such as humus, peat, sawdust or useful barks, also industrial products or byproducts such as perlite, various silicates, urea, etc. The solid formulations are then suitably diluted with a finely powdered mineral such as talcum.

The activity of the compositions of the present invention can be illustrated with the following Examples.

EXAMPLE 1

Wheat was soaked for 5 minutes in an aqueous solution containing in each liter 10 mg 1-heptadecenyl-2-aminoethyl-2-imidazoline. Subsequently the impregnated wheat carrier was sown and covered with a 7 cm thick soil layer and maintained for 8 weeks with water at half the normal rate. The solids content of the crop is 25% higher on marshy soil and 33% higher on argillaceous soil than controls. When water was applied at the full normal rate, the solids content of the plants was 18% higher on marshy soil and 14% higher on soda-containing soil than in the case of controls.

EXAMPLE 2

The test parcel contained soil comprising 85% quartzite with a 50–70 cm thick native soil layer and a ground water level of 1.5–2 m depth. The average temperature was 10.6° C. in April, 16.3° C. in May, 19.6° C. in June, 22° C. in July, and 21.1° C. in August. The area received 127 mm precipitation during the test period. The soil was treated at the rate of 10 kg/hectare with a mixture of N-oleoyldiethylenetriamide diacetate and a guanidine-formaldehyde condensate at a ratio of 4:1. The mixture was dissolved in 300 kg water. The control parcel was watered with the same amount of water. The active composition and the water, respectively, were worked into the ground in both parcels with a plow rake. Potato of the Pierwiosnek variety was planted in each parcel. On the test parcel treated with the active composition tuber formation occurred 3 days sooner, suberification occurred 5 days sooner, and ripening occurred 8 days sooner in the test parcel than in the control parcel. The yield increased by 18%, the number of tubers by 110% and at the same time they were 43% smaller than in the case of the control.

Other comparisons were made in connection with potatoes, with identical amounts of 1-isopropylnaphthaline-4-sulfonic acid sodium salt and with dodecylbenzoenesulfonic acid sodium salt, and also with anionic tensides. The yield was under identical conditions lower by 17% and 4.8%, respectively due to phytotoxicity. The 1-isopropylnaphthaline-4-sulfonic acid sodium salt does not affect the number of tubers, but only reduces the average weight thereof.

EXAMPLE 3

The sandy soil of Example 2 was treated before sowing with N-methylenecarbopalmitamide quinolinium bromide and with an aqueous solution of carboxymethylcellulose; the latter in an amount of 0.33 kg/hectare. Both chemicals are dissolved in 300 liters of water per hectare, then the solutions are divided and sprayed on the soil on two subsequent days. The control parcel was treated with plain water. After the second solution was applied to the test parcel, it was worked into the soil to a depth of 10 cm. Kecskemét rye (Hungary) was planted in the parcels. The test parcel showed an excess yield over the control parcel by 43.3%.

EXAMPLE 4

In the same sandy parcel as in Example 2 a similar experiment was carried out under the same weather conditions, with the exception that the active component was N-methylenecarbopalmitamide pyridinium bromide. 5 kg/hectare was employed. The resulting crop yield was 35% higher than in the case of the control parcel. The crop was tomatoes from a planting of midget tomatoes of the K-42-X, Kecskemét variety.

EXAMPLE 5

The procedure of Example 4 was repeated except that 5 kg/hectare of the following mixture was used: 20% by weight N-methylene-carbopalmitamide pyridinium bromide, 20% 1-aminoethyl-1-methyl-2-laurylimidazolinium iodide, 40% polyvinylalcohol, and 20% partially hydrolysed polyacrylamide. In the test parcel rye of the Kecskemét variety and midget tomatoes of the Kecskemét variety were planted. In comparison with the control parcel the yield was higher by 56.6% in the case of the rye, and by 78.3% in the case of the tomatoes.

EXAMPLE 6

The soil used in Example 2 was treated with N-palmitoylpropylenediamine diacetate on silica carrier in an amount of 1 kg/hectare. The active composition was worked into the soil to a depth of 10 cm. The control parcel was sprinkled with the same amount of pure water and this was also worked into the soil to the same depth. Corn was planted and the yield was 34.9% higher than in the case of the control parcel.

The experiment was repeated with anionic tensides. 0.66 kg/hectare dodecylbenzenesulfonate and also 1-isopropylnaphthaline-4-sulfonic acid sodium salt were spread over silica sand and then sprayed with an aqueous solution of polyethylene polyamine partially quaternised with an aqueous solution of acetic acid, in an amount of 0.34 kg/hectare. The chemicals were worked into the ground to a depth of 10 cm. Székács 8 (Hungary) variety of oats were planted into the control parcel and also into the test parcel treated with N-palmitoyl-propylenediamine. Dodecylbenzene sulfonate does not increase the yield and in the case of 1-isopropylnaphthalene-4-sulfonic acid sodium salt reduced the yield by 3.4% in comparison to the control.

EXAMPLE 7

In this Example a sandy soil was used having the following composition: 0.01% by weight $CaCO_3$, 0.34% humus, 1.0% ammonium, 1.65% nitrate, 10.6% absorbable $P_2O_5$, 4% absorbable $K_2O$. The water table was at 2–2.2 m depth. 102 mm precipitation was received on the test parcel during the experiment. During preemergence of the plants the parcel was with 6.6 kg/hectare of an aqueous solution of N-methylenecarbopalmitamide pyridinium bromide in 150 liters of water. The control parcel was sprayed only with plain water. Midget tomato seedlings of the Kecskemét K-42-X variety were planted. The yield in the test parcel was 20% larger than in the control parcel.

EXAMPLE 8

A loess-based 60–70 cm thick layer of carbon-containing brown forest soil containing 1.62% by weight humus, 1.85% ammonium, 0.8% $NO_3$, 2.2% absorbable $P_2O_5$, and 7.4% bound $K_2O$. After the deep ploughing in the fall and disc raking in the spring but before sowing, 1 kg/hectare in 300 liters/hectare of a composition containing 80% N-methylene-carbolauroxymorpholinium chloride and 20% guanidine-formaldehyde condensate was sprayed onto the soil of the test parcel and then worked into the soil to a depth of 20 cm. The control parcel was sprayed with water which was also worked into the ground. Beer barley (spring barley) of the Táplán (Hungary) variety was sown. 197 mm precipitation took place during the initial growth period as follows: 16.5 mm in April, 41.7 mm in May, 90.6 mm in June, and 48.8 mm in July. The average temperatures were 9.4° C. in April, 15.8° C. in May, 19.3° C. in June, and 21° C. in July. The crop yield in the test parcel was by 29% larger, and ear formation occurred 3 days sooner than in the control parcel.

Under identical conditions another control parcel was treated with sodiumdodecylbenzenesulfonate. No increase in yield occurred and the ear formation was delayed by 2 days in comparison to the test parcel.

EXAMPLE 9

Oats of the Székács 8 variety were sown under the same circumstances as in Example 8, at a chemical treatment rate of 5 kg/hectare. Ear formation occurred 3 days sooner and the increase in yield was by 32% higher than in the control parcel. On a control parcel treated with 5 kg/hectare sodiumdodecylbenzenesulfonate the increase in yield was not even ⅓ of that obtained on the test parcel, while in the case of another control, with 1-isopropylnaphthaline-4-sulfonic acid sodium salt the yield was reduced by 16%.

EXAMPLE 10

In this Example a loess-based 65 cm thick layer of forest soil was used, containing 0.03% by weight $CaCO_3$, 1.6% humus, 1.85% ammonium, 0.8% nitrate. The total precipitation during the test period was 198 mm: 16.5 mm in April, 45.7 mm in May, 90.6 mm in June, and 48.8 mm in July. The average temperatures were 9.4° C. in April, 15.8° C. in May, 19.3° C. in June, 21° C. in July, and 20° C. in August.

After deep ploughing in the fall, and cultivation in the spring, the soil was treated with an aqueous solution of N-methylenecarbopalmitamide quinolinium bromide composition which comprised 3.3 kg of the active compound applied onto 16.5 kg/hectare of Neuburg chalk as carrier suspended in 300 liter/hectare of water, with 0.66 kg/hectare octadecaglycol-oleoyl ester, as suspending agent. One day later the soil was treated with an aqueous solution of 6.6 kg carboxymethylcellulose and 150 liter of water/hectare. The control parcel was treated with the same amount of plain water. Maize of the MV-5 variety was planted into the parcels with the square planting method. The yield on the test parcel was by 17.6% higher than on the control parcel.

EXAMPLE 11

The composition of the soil and the weather conditions in this Example were the same as in Example 10. 3 kg/hectare of 1-aminoethyl-1-methyl-2-lauryl-2-imidazolinium acetate on 12 kg silica carrier were worked into the soil to a depth of 10 cm. Potatoes of the Pierwiosnek variety were planted. Due to the treatment of the test parcel spud formation commenced 5 days sooner, suberification 8 days sooner and ripening 11 days sooner than in the control parcel. The harvest on the test parcel was 31.3% higher, while in comparison on the control parcel the number of spuds was about 16.4% fewer, but about 57% larger. This method of treatment, therefore is especially suitable for potatoes for human consumption.

EXAMPLE 12

Brown forest soil was treated with a mixture of active ingredients and fertilizer. The experiment was carried out with N-methylene carbolauroxy morpholinium chloride and with 60% N-oleoyl-diethylenetriamide borate, 30% bis-N-lauroyl diethylenetriamide, 10% urea-formaldehyde condensate, respectively. The components were dissolved in water in a 1:60 ratio, and 300 liter/hectare. The yield increases which were obtained under average conditions, are summarized in the following table.

| Ingredient | Add'l. yield in %, compared to the control | | | | |
|---|---|---|---|---|---|
| | Super-phosphate | K | K-urea | $NH_4 NO_3$ | Ca nitrate |
| N-methylene-carbolauroxy-morpholinium chloride | 19.5 | 12.5 | 4.8 | 19.1 | 16.8 |
| N-oleoyldiethylene triamide + 30% N-lauroyl-diethylenetriamide + 10% urea-formaldehyde condensate | 23.7 | 7.9 | 9.3 | 15.4 | 18.1 |

The control parcels were treated only with fertilizers. From the results it is clear that the active components of the invention are not substitutes for fertilizer but exert an additive growth effect independently therefrom.

EXAMPLE 13

Soil of the same type as in Example 12 was treated under identical conditions with 6.6 kg/hectare of N-palmitoylpropylenediamine on silica gel carrier. After spreading the material onto the soil, it was worked in to a depth of 10 cm, and maize of the MV-5 variety was planted with the quadratic method in the parcels. The yield was by 18.5% higher in the test parcel than in the control parcel.

EXAMPLE 14

The same soil as in Examples 12 and 13 was treated under identical conditions with 3.33 kg/hectare N-methylenecarbolauroxy pyridinium chloride and 1.67 kg/hectare 1-aminomethyl-2-lauryl-2-imidazoline. The actives were applied to a perlite byproduct carrier. The composition was worked into the soil to a depth of 10 cm and then maize of the MV-5 variety was planted with the quadratic system. In comparison with the control parcel, the yield was 26% higher.

The experiment was repeated under identical conditions, except that the individual compounds were separately used in the same amounts. Also in this case the ingredients each were applied onto a perlite byproduct carrier before spreading onto the soil. The yield increase in the case of N-methylenecarbolauroxy pyridinium chloride was about 12.3% and in the case of the 1-aminoethyl-2-laurylimidazoline was 7.1%. In this Example the synergism of the combined ingredients was demonstrated.

EXAMPLE 15

On the same soil and under identical weather conditions as in Examples 12–14 and after identical soil preparation an aqueous solution of 1 kg/hectare cetyltriethylammonium bromide and 2 kg/hectare 1-ethylamino-2-oleyl-2-imidazoline and 1 kg/hectare guanidine-formaldehyde condensate in a mixture was applied. The control was treated with an identical amount of water. Both the water and the actives were worked into the soil to a depth of 10 cm. Maize of the MV-5 variety was planted with the quadratic system. The yield increase in maize grains was 16% and in green plant components about 10%.

EXAMPLE 16

The same soil as in Example 12–15 was treated under identical conditions, with 600 kg/hectare NPK fertilizer and also with 3 kg/hectare N-cetoylpropylenediamine borate on silica carrier. The materials were worked into the soil to a depth of 10 cm. Sugar beets were planted of the variety Beta Polly 3. The yield increase in comparison with the control parcel was 32% with respect to the beets and the increase in sugar content was of the same relative percentage.

EXAMPLE 17

The same soil as in Examples 12–16 was treated under the identical conditions, with 600 kg/hectare of NPK fertilizer, whereby the fertilizer also served as carrier for 6 kg 1-aminoethyl-1-methyl-2-cetyl-2-imidazolinium iodide. Feed grade peas were planted. The yield increase for peas was 21% higher than in the control parcel which was treated only with 600 kg/hectare NPK fertilizer. The peas of the test parcel contained 6.8 relative percentage points more protein than those of the control parcel.

EXAMPLE 18

In these experiments the soil was layered on loess loam, the soil being an 85 cm thick layer having a composition of 1.68% $CaCO_3$, 0.75% humus, 1.07% ammonium, 1.77% $NO_3$. The water table was at 180–190 cm depth. The average temperatures were 16.9° C. in May, 19.8° C. in June, 21.5° C. in July, and 20.5° C. in August. The total precipitation during this period was 113 mm, as follows: 12 mm in May, 83 mm in June, 13 mm in July and 7 mm in August.

After deep ploughing in the fall and cultivation in the spring maize of the MV-620 variety was planted with a hand spreader by the quadratic method. Thereafter 1 kg/hectare of material in 300 liter/hectare water of the following composition was applied to the soil of the test parcel: 6/10 part bis-oleoyl-diethylenetriamide, 3/10 part lauroyldiethylenetriamide diacetate, 1/10 part 1-aminoethyl-2-hexadecyl-2-imidazoline. The control parcel was watered by plain water. The treating material and water, respectively, were worked into the soil to a depth of 8–10 cm. In comparison with the control, the yield increase was 15% and with respect to maize straw 6%.

When an anionic tenside such as sodiumdodecylbenzenesulfonate was used to treat the soil, under identical circumstances only a 3% yield increase was obtained and the maize straw yield was lowered by 6%.

EXAMPLE 19

6 kg/hectare N-ethylene-carbolauroxyquinolinium iodide solution is sprayed onto a dry soil on a loess base. A week killer is also applied to the soil at the same time. These agents are tilled into the soil and then a MBTC 431 type corn is planted. During the growing period 210 mm precipitation took place. In the treated parcel a 17.4% higher crop yield was obtained as compared with a similarly handled but untreated control parcel.

EXAMPLE 20

10 kg/hectare N-ethylene-carbomyristicamidequinolinium bromide was sprayed in an aqueous suspension onto 60–70 cm thick soil on a clay base. The suspension was prepared by mixing each hundred kilogram of active ingredient in hundred kilograms of sunflower oil and emulsifying the resultant mixture with 10 kilograms of polyethyleneglycol ether in 1 cubic meter of water. After spraying, the emulsion was tilled into the soil and rye was planted. During the growing period 192 mm precipitation took place. In the treated parcel the yield was 16.7% higher than in the untreated control parcel.

EXAMPLE 21

A solution of 5 kg/hectare N-propylenemyristic amidepyridinium bromide, in 300 liters/hectare water, was sprayed onto a clayey sandy soil on a rock ledge base and then fall wheat was planted. In the spring, simultaneously with the spraying of fertilizer, the plants, which were becoming bushy, were also sprayed with the solution but it was not tilled into the soil. Between the spring spraying and harvest, 237 mm precipitation fell. The grain crop yield in the treated parcel was 21.4% higher than in the untreated control parcel. The total protein content of the wheat was 3.6% higher in the treated parcel than in the control parcel. The chaff proportion was basically the same in both the treated and untreated parcels.

EXAMPLE 22

A mixture containing 10 kg/hectare of N-methylenemyristicamide-pyridiniumbromide, and 100 kg/hectare silicagel carrier, was spread dry onto a brown forest soil on clayey soil base, then tilled 20–25 cm deep and turned into the soil. Then sugar beet was planted. Between the treatment and harvesting, 293 mm precipitation fell. The sugar beet yield was 32% higher in the treated parcel than in the untreated control parcel. The dry material content of the beat was 9.7% higher and the sugar content 3.2% higher in the crop obtained in the untreated parcel. The increase in sugar content is, however, not significant.

EXAMPLE 23

On a sandy soil, having a humus content of 1.02%, a growth of grapes was standing. In the spring, before the grapes blossomed, 15 kg/hectare N-methylenecarbolauroxypyridinium chloride, in a solution of 300 liters/hectare water, was sprayed onto the soil. By harvest time, at the end of August, a total of 227 mm precipitation had fallen. The crop yield in the treated parcel was 11.5% higher than in the untreated control parcel.

EXAMPLE 24

10 kg/hectare N-methylenecarboleyloxy-pyridinium acetate, in an aqueous solution, was applied to a clayey soil. Tobacco of the Kallo-type was planted and during the growth period 334 mm precipitation fell. An 18.7% higher yield was obtained in the treated parcel than in the untreated control parcel. The tobacco obtained from the treated parcel had a lighter color than that obtained from the untreated control parcel. The following year, when less precipitation fell, viz. 102 mm, similar treatment of the test parcel resulted in a 48% increase in yield than in the untreated control parcel.

EXAMPLE 25

6 kg/hectare N-ethylenecarbolauroxyquinolinium nitrate, in aqueous solution, was sprayed on acidic forest brown soil. Wheat was planted in the treated parcel. In the spring, when the plants began to become bushy and simultaneously with the customary fertilization, an additional 6 kg/hectare N-ethylenecarbolauroxyquinolinium nitrate was sprayed on the soil. Care was taken to avoid trampling the growing plants with the equipment utilized. During the growth period, 287 mm precipitation fell. In the treated parcel the yield of grain was 15.8% higher than in the untreated control parcel.

EXAMPLE 26

10 kg/hectare N-propylenecarbolinoxy-morpholinium acetate and 50 kg/hectare hydrolized polyacrylonitrile sodium salt, in 300 liter/hectare water, was sprayed onto solonyez-type meadow soil. After spraying, MV 580-type corn was planted. From the time of treatment until breaking of the corn, 317 mm precipitation fell. In the treated parcel, the crop yield was 15.6% higher than in the untreated control parcel. Moreover, in the treated parcel the dry material content of the crop was 9.8% higher than in the untreated control parcel. Thus the total dry weight increase of the treated parcel was 26.9% higher than in the untreated control parcel.

EXAMPLE 27

A 1:1 emulsion of sunflower oil was prepared with N-hexylenecarbo-11,11-dimethyllauroxymorpholinium acetate, with a polyethyleneglycol oleylester. This emulsion was sprayed onto brown forest soil. The total amount of the active and the sunflower oil was 12 kg/hectare and the polyglycol ester emulsifier was 2 kg/hectare. 100 liters per hectare water were employed in the preparation of the emulsion. After application of the emulsion to the test parcel, a Kecskemét midget type tomato was planted. Water corresponding to a daily precipitation of 15 mm was sprayed during the first six days of the treated parcel and on the control parcel. From then on 173 mm natural precipitation fell. The ripening of the tomato took place eight days sooner on the treated parcel and took seventeen days longer than on the control parcel. The yield in the test parcel was 21.7% higher than in the untreated control parcel.

EXAMPLE 28

A dry brackish, meadow soil was treated with a 10 kg/hectare N-butylenecarbo-6-hexyl-lauramide-pyridinium sebacate, which was applied to 15 times its weight of silica gel. The active applied to the carrier was suspended with 8 kg/hectare polyvinylpyrrolidone in 500 liters/hectare water then sprayed onto the soil. the spray was turned into the soil and then alfalfa was planted. After the first mowing the alfalfa was 19.7% higher, on the second mowing 16.3% higher, on the third mowing 15.8% higher in green mass on the treated parcel than on the untreated control parcel. The total increase on the treated parcel in the first year was 17.1%. In the second year the treatment was repeated in the spring but the active substance was not applied to a carrier but emulsified in an amount of 10 kg/hectare in 150 liters/hectare water with 2 kg/hectare polyvinylpyrrolidone. After the treatment, the rain washed the material into the soil. In the second year, on the first mowing 21.3%, on the second mowing 20.0%, and on the third mowing 18.2%, a total of 20.1% increase in green mass was obtained in the treated parcel in comparison to the untreated parcel.

EXAMPLE 29

A clayey sand soil was treated with 6 kg/hectare N-ethylenecarbostearoxy-phenanthradinium tartrate dissolved in 300 liters/hectare water. Sunflower seeds were planted. 312 mm precipitation fell during the growing season. Grain yield was 17.8% higher in the treated parcel than in the untreated control parcel. Moreover, the acid number of the oil pressed from the sunflower on the treated parcel was lower by 9.

EXAMPLE 30

The same soil as described in Example 29 was sprayed with 6 kg/hectare N-hexylene-3',6'-dion-lauroxy-5,6-dimethylpyridinium propionate dissolved in 300 liters/hectare water. Pierwiosnek potato was planted. 287 mm precipitation fell during the growing season. The potato cropyield was 22.3% higher in the treated parcel, than in the untreated parcel. The increased yield was primarily attributable to the fact than in the treated parcel the individual potatoes were generally larger. The yield of exportable pomme fritte-grade potatoes in the treated parcel was 10% higher than in the untreated parcel. Moreover, the proportion of fodder grade potatoes was 10% lower in the treated parcel than in the untreated parcel.

EXAMPLE 31

Meadow soil was treated with 10 kg/hectare N-decylene 2',4',6',8',10' pentane lauramide pyridinium acetate. The material was first applied to 50 kg/hectare of finely ground loam carrier and was suspended in 150 liters/hectare water with 2 kg/hectare polyvinylpyrrolidone before application to the soil. After spraying, it was turned and tilled 15 cm deep. Hemp was then planted. 295 mm precipitation fell during the growing period. The gathered green mass was 5.6% higher, the fibrous mass 9.7% higher, and the amount of fibre was 11.8% higher in the treated parcel than in the untreated control parcel. Moreover, fibres obtained from the treated parcel were of a finer grade.

EXAMPLE 32

5 kg/hectare N-hexylene-3',6'-dion-oleoamide-5-methylpyridinium hydrogen carbonate was applied to 500 kg/hectare manure and the resultant combination applied to eroded tshernozyom soil. The control parcel was treated with 500 kg/hectare manure and no active was applied. The manure was tilled into the soil on both tracts to a depth of 25 cm and winter wheat was planted. In the spring, the test parcel was again sprayed with 5 kg/hectare N-hexylene-3',6'-dionoleoamide-5-methylpyridinium hydrogen carbonate in 150 liters/hectare water with 2 kg/hectare polyvinylpyrrolidone emulsifier while the control parcel was sprayed with 150 liters/hectare pure water. During the growing season 233 mm precipitation fell. The green yield was 17.3% higher in the treated parcel than in the untreated control parcel.

EXAMPLE 33

A growth of Mariska-type peach trees were standing on a clay soil. This soil was treated with N-ethylenecarbolauramide-pyridinium carbonate in an amount of 15 kg/hectare active dissolved in 150 liters/hectare water. 197 mm precipitation fell during the growing season. After the customary scarifying, the growth was 17.5% higher in the treated parcel than in the untreated one. This was mainly due to the larger size of the peach crop on the treated parcel.

EXAMPLE 34

Marshy soil was treated with a suspension of 3.5 kg/hectare N-ethylene-carbolinoleicamide-6-methyl-morpholinium phosphate, 1.5 kg/hectare glue and 300 liters/hectare water. Carnations were planted, then the soil was watered as if it would have received 60 mm precipitation per month. In the parcel treated with the active material the flower yield was 7.3% higher than in the untreated parcel. Moreover, in the treated parcel, the average size of the flowers was 1.7 cm larger than in the untreated parcel.

EXAMPLE 35

10 kg/hectare N-butylene-2',4'-dion-stearoxy-2-methylquinolinium butyrate was applied to 150 kg/hectare calcium carbonate powder and the resultant combination was dusted onto solonyez type meadow soil then tilled into the soil to a depth of 25 cm. 150 kg/hectare calcium carbonate powder, without the active, was also tilled 25 cm deep into the soil of the control parcel. MV 620-type silo maize was planted. 274 mm precipitation fell during the frowing season. The green yield was 19.2% higher in the treated parcel than in the untreated control parcel.

EXAMPLE 36

Clayey soil was treated with 6 kg/hectare N-hexylene-2'',4'',6''-trion-11',11'dimethyl-linoxy-5,6-dimethylpyridinium nitrate solution. The solution was prepared by mixing the active in a 1:1 ratio with sunflower oil and then suspending it with 1.5 kg/hectare polyvinyl pyrrolidone in 150 liters/hectare water. The solution was sprayed on then turned into the soil to a depth of 6–10 cm. Peas were then planted. The blooming, pod formation, and ripening of the peas in the test parcel occurred one week sooner than in the untreated control parcel. The green yield was 22.3% higher in the treated parcel than in the control parcel. The fodder value was also 19.7% higher in the test parcel.

EXAMPLE 37

Small parcel experiment was made in fourfold repetition on a solonyez type soil. The active substance was N,N,N-triethyl-ammonium-N-tetramethylenetetraminedecanoic acid-N''''-amide formiate of the following formula

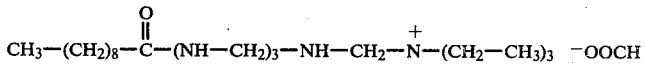

A dose corresponding to 37 kg/hectare was mixed in a ball mill with 2000 kg of sand. The sandy composition was sprayed on the soil to be treated. The composition was incorporated into the soil into a depth of 5 cm. The control parcels were treated with 2000 kg/hectare of sand without active substance and this dose has been also worked into the soil. For comparison purposes 100 kg/hectare of polyacrylic amide as a soil conditioner was used as well and this soil conditioner was worked into the soil. The treatment was made before the sowing of the plant. Thereafter sugar beet was sown and the amount of precipitation was between the period of sowing and harvesting about 298 mm. Applying the composition containing the active substance the yield was 22.7% higher than the control. The parcels treated with polyacrylic amide soil conditioner yield a surplus amounting to 9.2% compared to the control. The result obtained with the above active substance proved significant on a 1% of probability level whereas the results obtained with polyacrylic amide only on a 10% probability level.

EXAMPLE 38

Small parcel experiments were made in sixfold repetition on a brown forest soil with alfalfa. Two kinds of active substances have been used. The first one was the N-isopropyl-tetraethylenepentamine dec-5-anoic acid-N'''''-amide of the formula

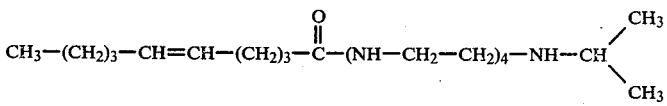

The second one was N-(7-hexyl-dodecyl)-ammonium-N-butyl-4'-amine-octadeca-6,12-dienoic acid amide butyrate of the formula

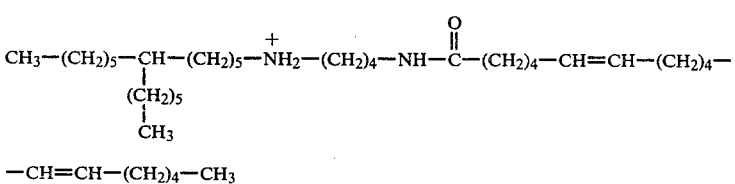

The dose of the first active substance was 19 kg/hectare and this dose was mixed with 6 kg/hectare of ethanolamine and the mixture was emulgated under the exclusion of air in a colloid mill with 275 liters/hectare of water. 300 kg/hectare of the emulsion was sprayed on the soil.

The second active substance was mixed in a ratio of 1–20 with a highly crosslinked urea-formaldehyde condensate which was used in a dose amounting to 88 kg/hectare. After homogenization the mixture was milled into a fine grain size and together with 5% by weight polyglycol ether it was suspended in a fivefold amount of water. The suspension was sprayed on the soil in an amount corresponding to 1.16 mm precipitation.

After treating the soil with the active substance it was incorporated in depth of 10 cm, thereafter alfalfa was sown. The amount of precipitation was in the first year 475 mm, in the second year 423 mm. The experiment with alfalfa was performed for two years. In the first year alfalfa was cut down three times in the second year four times.

The result of these treatments based on the untreated control expressed in yield surplus percentage are the following:

| First year: | | |
|---|---|---|
| | first cut down | 116.7 |
| | second cut down | 122.5 |
| | third cut down | 123.8 |
| | mean | 122.9 |
| Second year: | | |
| | first cut down | 112.2 |
| | second cut down | 117.3 |
| | third cut down | 120.9 |
| | fourth cut down | 119.5 |
| | mean | 119.3 |

The yield surplus proved using both active substances significant on an 1% probability level.

EXAMPLE 39

Middle parcel experiment was made in fourfold repetition with grapes on a sandy soil with fruit-bearing grape. The active substance used in this experiment was N,N-dilinolil-ammonium-N-hexaethylenehexamine dodec-6-anoic acid amide nitrate of the formula

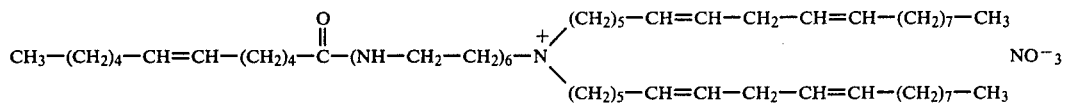

The soil was sprayed with the emulsion in spring-time before budding. An amount of 1295 liters/hectare of the emulsion was sprayed on the soil. In the period of the treatment and the vintage the soil received a precipitation of about 327 mm. The yield was with 31.0% higher in the treated parcels than in the control parcels. The yield surplus proved significant on a 1% probability level.

EXAMPLE 40

An experiment on large scale was carried out with maize and open country soil was used. The active substance utilized was N,N-dipalmitylamino-N-dipropylene-di(methylammonium)-N'''-propyleneamine-decanoic acid-N''''-amideiodide of the following formula

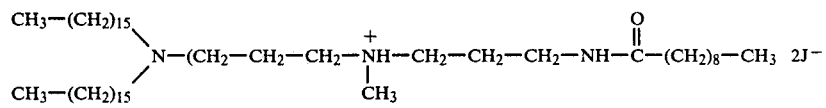

126 kg of active substance was homogenized with 12.6 kg of linolic acid, thereafter the homogenized mixture was sprayed on 1380 kg of diatomic earth as a carrier and the whole mixture was milled. The milled mixture was sprayed via pre-sowing method on the surface of the soil, thereafter the soil was treated post-emergence with a fertilizer and weed killer. The substances used in the course of the various treatments were worked into the soil by means of discing, thereafter pea was sown in the soil. In the period between sowing and harvesting, the precipitation amounted to 318 mm. The average yield was with 19.3% higher than in the control soil.

EXAMPLE 41

A small parcel experiment was carried out in sixfold repetition on a solonyez-type meadow soil. The used active substance was tetraethylene pentamine-tetra-eicosanoic acid-amide of the following formula

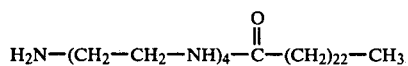

The active substance was melted on a temperature not higher than 80° C., thereafter was thoroughly mixed with a threefold amount of urea. Under stirring gypsum peptised in water was mixed into the urea-active substance mixture using an amount of gypsum corresponding to the fourfold amount of the active substance. The amount of water was twice more than the amount of the active substance. The components were homogenized and the gypsum was left to solidify. Under the action of gypsum the whole system solidified, the solid mixture was milled to a fine grain size. 168 kg of the above mixture per one hectare was sprayed on the soil and together with manure it was worked into the soil by ploughing. After ploughing winter wheat was sown into the soil. Between the period of sowing and cultivation in spring-time the precipitation amounted to 199 mm. In the course of the cultivation an amount of 84 kg of mixture per hectare was sprayed on the surface of the soil without working it into the soil. In the period between the agricultural treatment in spring-time and harvesting the crop the precipitation amounted to 230 mm. The yield of the crop was 21.7% higher in the treated parcels than without the treatment and the obtained result proved significant on an 5% probability level.

EXAMPLE 42

Small parcel experiment was carried out with tomato on a brown forest soil in sixfold repetition. The utilized active substances were the following:

bis-N,N'-(tetraeicosyl-8,16-dienone)-1-aminoethyl-oxyethylamine of the formula:

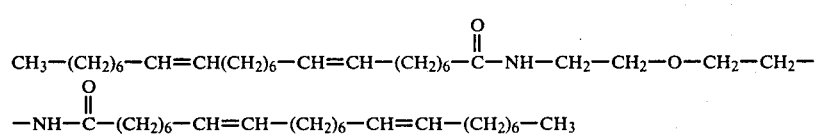

The second active substance was N,N,N-trihexylammonium-N-hexamethylenehexamine-6-hexyl-lauric acid-N''''''-amidehydroxide of the formula

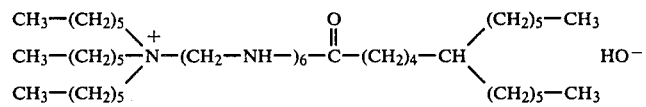

The first active substance was emulgated in water in a colloid mill at 80° C. with an emulgator of polyglycolether type which was used in an amount of 8% based on the active substance. The concentration of the aqueous emulsion was adjusted to 20%. The second active substance was emulgated with 3% glue and 5% methylene carbolauroxypiridiumamide as an emulsifying agent. The concentration of the second emulsion was adjusted similarly to 20% active substance. The emulsions were sprayed in an amount of 600 liter/hectare on the soil, thereafter the emulsion was worked into the soil by means of raking and tomato was sown into substance was N-palmityl-ammonium-N-tetraethylenetetramine 10-(dec-5'ene) eicos-5,15-dienoic acid-N''''''-amide of the formula

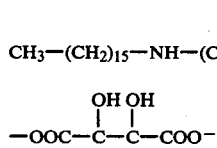
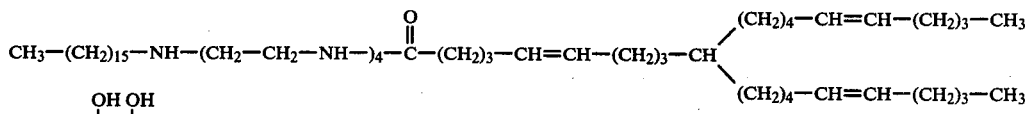

the soil. After bedding out the plants irrigation was used according to the water requirement of the plants. Between bedding and the first harvesting the soil received a precipitation of about 217 mm, whereas between bedding out and the last harvesting the amount of precipitation was altogether 293 mm. The obtained yields based on the untreated control and expressed in percentage were the following:

|  |  |
|---|---|
| first active substance | 128.3% |
| second active substance | 127.2% |

Both results proved significant on an 5% probability level.

EXAMPLE 43

Pot experiment were carried out in 16-fold repetition, in a glass house using air ventillation with control fed temperature and artificial u.v. light. The irrigation was controlled in a manner that the plants should obtain an amount of water slightly more than that of corresponding of the wilting point of the plant. The soil was a loamy one. The used active substance was 3-aminopropyl-3'-oxypropyl-3''-oxypropylamine-eicosenoic acid-N'-amide of the formula

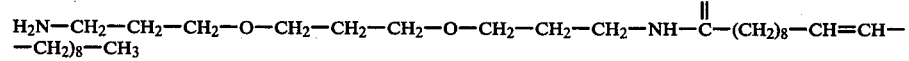

The active substance was melted and sprayed on silica gel, thereafter the silica gel was pulverized. The active substance content of the mixture was 10% and the composition was suitable for suspension. Before using the active substance it was suspended in water, the suspension was applied with a 20% active substance concentration. The suspension was sprayed in a dose amounting to 2250 liters/hectare on the surface of the soil. Thereafter 10 grains of bean were placed in a depth of 2 cm. under the soil surface. The experiment was performed for 8 weeks and at the end of the experiment the amount of the green mass was measured. The yield was with 31.6% higher in the treated parcels than in the untreated control pot parcel. The surplus proved significant on an 0.1% probability level. It should be noted that the sprouting of the treated plants was 98.7% in contrast to the untreated control which was only 83.5%. In addition the period of time until blossoming could be shortened with 4-5 days.

EXAMPLE 44

Small parcel experiments were made in four repetition on a soil of tshernozyom-type. The used active The active substance was mixed with 3% of glue, 3% of ethanolamine and 5% of an emulsifier of polyglycolether type at 60° C. and it was emulgated in water using a colloid mill. The emulsion contained 20% of active substance. This composition was used to treat winter wheat in an amount of 460 liters/hectare, applying the composition on the surface of the plant. At the beginning of the budding in the period between the treatment and the harvesting the amount of the precipitation was 101 mm. The yield on the treated parcels was with 27.3% higher than on the untreated control. The result proved significant on an 5% probability level.

EXAMPLE 45

Large scale experiment was carried out on a meadow soil the size of the parcel was about 10 hectares. The active substance was N-triethylammonium-N'-ethyleneethylammonium-eicosanoic acid amide phosphate of the formula

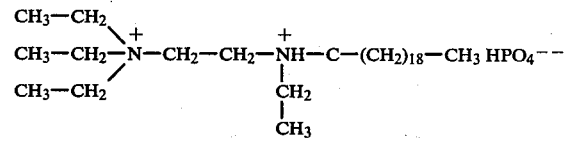

The active substance was emulgated using an emulsifier of the methylenecarbolauroxy piridinium bromide type and the active substance was emulgated in a colloid mill. The emulsion contained 20% of active substance. The composition was used in an amount of 300 liters/hectare, together with a liquid fertilizer. The active substance was worked into the soil in a depth of 10 cm and thereafter maize was sown. In the period between the treatment and harvesting the amount of precipitation was 313 mm. The average grain yield of the treated plots was higher with 19.8% than that of the untreated plots.

EXAMPLE 46

Small parcel experiments were carried out on a sandy soil in sixfold repetition. The utilized active substances were the following:
(1) N-methylketonamine-N-ethyl-1'-oxyethyl-aminoethyl-1''-oxyethyl-N''-ethylammonium-lauric acid-N''-amidebromide of the formula

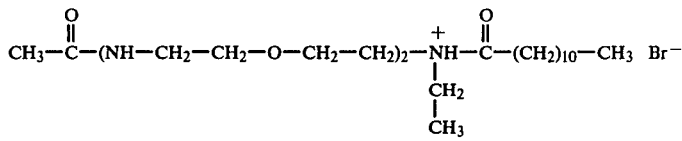

(2) amino-[tetraethylenetetra-(decylammonium)]-ethyleneamine-decanoic acid-N'''''''-amide-bromide of the formula

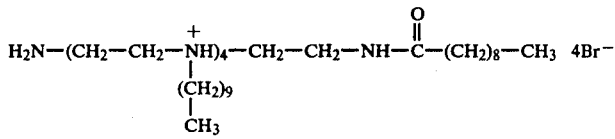

The first active substance was mixed in an 1:10 ratio with diatomaceous earth and the mixture was milled. The second active substance was dissolved in ethanolamine and was sprayed on pulverised calcium carbonate. The solvent was distilled off in vacuo and recovered. The amount of active substance was about 9% of the carrier substance. The test parcels were treated with 338 kg of the active substance and 545 kg of the second active substance based on one hectare soil. The compositions were worked into the soil, thereafter potato was planted. In the period between planting and harvesting the amount of precipitation was 279 mm.

The obtained yields based on the untreated control and expressed in percent were the following:

| | |
|---|---|
| first active substance | 121.9 |
| second active substance | 123.2 |

The yields surplus proved significant on an 1% probability level.

EXAMPLE 47

Small parcel experiments were carried out with fodder pea on sandy brown forest soil. The used active substance was N,N-diethyl-amino-[pentakis-(N',N'',N''',N'''',N''''')-ethyl-oxyethyl-hexadecinamino]-ethyl-oxyethylaminepalmitoyl-N'''''''-amide of the formula

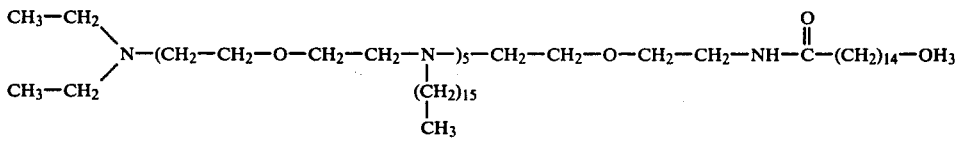

The active substance was melted with carnauba wax and left solidified. The weight ratio of active substance and of the wax was 1:5. After solidification the mixture of the active substance and the carnauba wax it was milled in a ratio of 1:1 with sand and thereafter was spread on the soil in a dose in amounting to 1100 kg/hectare. The composition was worked into the soil and fodder pea was planted. In the period between planting and harvesting the amount of the precipitation was 293 mm. The grain yields of the treated parcels were 19.8% higher than that of the untreated controls. The result proved significant on an 5% probability level.

EXAMPLE 48

Small parcel experiments were made in 4-fold repetition with maize on a meadow soil of solonyez-type. The utilized active substances were the following:
    1-oxyethyl-2-trieicosil-2-imidazoline and 2 nonyl-imidazoline.

The first active substance was dissolved in fivefold amount of ethanolamine and was used in solution.

The second active substance was incorporated into rape oil and was used in form of an emulsion. The spraying was carried out according to the pre-sowing method. The utilized dose was in case of the first active substance 67 kg and in case of the second 30 kg/hectare. The compositions were worked into the soil, thereafter maize was planted. In the period between planting and harvesting the amount of the precipitation was 276 mm. The yield based on the untreated control and expressed in percent were the following:

| | |
|---|---|
| first active substance | 130.8% |
| second active substance | 128.1% |

The yield surplus proved significant on an 1% probability level.

EXAMPLE 49

Small parcel experiments were made on a loamy sandy soil with the following active substances:
    1,1-dipropyl-2-nonenyl-2-imidazolinium-nitrate and
    1-oxypropyl-2-heptadecenyl-2-imidazolinium-formiate.

The tests were made in fourfold repetition. The active substances are water soluble and were used in 5% solution. The dose was 100 liters/hectare of the solution. The solutions were worked into the soil and potato was planted. In the period between sowing and harvesting the amount of precipitation was 412 mm.

The yield surplus based on the untreated control and expressed in percent were the following:
first active substance (325 metric centner/ha. = 115.6%)
second active substance (341 metric centner/ha. = 121.3%)
    untreated control (281 metric centner/ha. = 100%).

The yield surplus proved significant on an 5% probability level.

EXAMPLE 50

Large scale test were carried out on a soil of tschernozyom-type which was subjected to strong erosion. The size of the treated soil was 50 hectares and from this area 10 hectares was treated according to the invention and 40 hectares of the area was left untreated. The plant used was sugar beet and the active substance was mixed with 10% ethanolamine, and the solution of the active substance was sprayed on milled perlite and milled further in a ball mill. The active substance was in the case 1-ethyl-2-undecenyl-2-imidazoline. The weight ratio of active substance and perlite was 1:5. Thereafter 61 kg/hectare was spread on the surface and alfalfa was planted. The alfalfa was cut down 3 times in the first year and 4 times in the second year. At the beginning of the second year the treatment was made post-emergence similar to the first treatment.

The obtained yields expressed in dry matter content based on the untreated control were the following:

| first year | | | |
|---|---|---|---|
| | first cut down | | 118.7 |
| | second | | 123.9 |
| | third | | 125.9 |
| | | mean | 124.1 |
| second year | | | |
| | first cut down | | 130.8 |
| | second | | 131.1 |
| | third | | 129.8 |
| | four | | 127.6 |
| | | mean | 129.1 |

Yield surplus of two years in the average 127.8.

EXAMPLE 52

Small parcel experiments were made in sixfold repetition on a brown forest soil with flax. The used active substance was 1-aminopropyl-1-ethyl-2-trieicosenil-2-imidazolinium chloride. The active substance was brought into colloidal solution with a fivefold amount of water, thereafter it was mixed with silica gel which was used in a fivefold amount of the active substance. The obtained humid mass was dried and milled to a fine grain size. The composition was used in a dose corresponding to 80 kg/hectare and was worked into the soil. In the period between treatment and pulling the precipitation amounted to 412 mm. The surplus yield in flax based on the untreated control was 118.7% and this result proved significant on an 5% probability level.

What we claim is:

1. A method for increasing plant yield comprising applying to the soil in which the plants are to be grown, an amount effective to increase the yield of said plants of a cationactive compound of the formula I

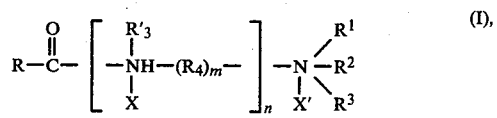

wherein R is a $C_{10-24}$ linear or branched alkyl, alkenyl or alk-dienyl-group; $R_1$ is hydrogen, $R_2$ is hydrogen, $C_{2-18}$ is a linear or branched alkyl, alkenyl, alk-dienyl or $C_{2-18}$-alpha-keto-group, $R_3$ is a hydrogen; $R_3'$ if present is hydrogen or $C_{1-8}$ alkyl; X and X' are formiate, acetate, propionate, hydrophosphate, hydroxyl, halogen or nitrate; $R_4$ methylene, ethylene or a polyglycolether-group; m is a cardinal number from 1–6 and n is an integer from 1–6; and a chemically compatible solvent, dispersing agent or carrier therefore.

2. The method as claimed in claim 1, wherein said cationactive compound is applied to the soil in an amount of from 1 kg to 100 kg per hectare.

3. The method as claimed in claim 1, wherein said cationactive compound is applied to the soil in an amount of from 5 kg to 10 kg per hectare.

* * * * *